United States Patent
Milosevic et al.

(10) Patent No.: US 8,953,034 B1
(45) Date of Patent: Feb. 10, 2015

(54) VIDEO IMAGING DEVICE WITH AN INTEGRATED BATTERY

(76) Inventors: Milan Milosevic, Westport, CT (US); Violet Milosevic, Westport, CT (US)

( * ) Notice: Subject to any disclaimer, the term of this patent is extended or adjusted under 35 U.S.C. 154(b) by 1204 days.

(21) Appl. No.: 11/805,184

(22) Filed: May 22, 2007

Related U.S. Application Data

(60) Provisional application No. 60/802,664, filed on May 23, 2006.

(51) Int. Cl.
*H04N 5/253* (2006.01)
*H04N 7/18* (2006.01)
*G01N 21/88* (2006.01)
*G01N 21/01* (2006.01)

(52) U.S. Cl.
CPC ............ *G01N 21/8806* (2013.01); *G01N 21/01* (2013.01)
USPC .......................................................... 348/92

(58) Field of Classification Search
CPC ..................... G05B 2219/2615; G06F 3/0481; G01N 21/01; G01N 21/8806
USPC .......................................................... 348/92
See application file for complete search history.

(56) References Cited

U.S. PATENT DOCUMENTS

| | | | |
|---|---|---|---|
| 1,370,645 A | 3/1921 | Hawkes | |
| 2,146,906 A | 2/1939 | Moller | |
| 2,557,029 A | 6/1951 | Griffin | |
| 3,286,353 A | 11/1966 | Potter | |
| 3,571,934 A | 3/1971 | Buck, Sr. | |
| 4,118,871 A | 10/1978 | Kirkham | |
| 4,281,385 A | 7/1981 | Nakaso | |
| 4,438,567 A | 3/1984 | Raiha | |
| 4,831,438 A * | 5/1989 | Bellman et al. | 348/148 |
| 4,884,878 A | 12/1989 | Arenal | |
| 5,486,853 A * | 1/1996 | Baxter et al. | 348/222.1 |
| 6,221,007 B1 * | 4/2001 | Green | 600/160 |
| 6,640,145 B2 * | 10/2003 | Hoffberg et al. | 700/83 |
| 7,006,881 B1 * | 2/2006 | Hoffberg et al. | 700/83 |
| 7,021,160 B2 * | 4/2006 | Pattok et al. | 73/862.332 |
| 7,966,078 B2 * | 6/2011 | Hoffberg et al. | 700/17 |
| 2007/0208766 A1 * | 9/2007 | Malik | 707/101 |

* cited by examiner

*Primary Examiner* — Kristie Shingles

(57) ABSTRACT

A compact, battery powered video imaging device for use in XYZ stage equipped machines (such as milling machines, jig borers, coordinate measuring machines, etc.) that mounts into the spindle of such a machine and displays a magnified image of a part on the XYZ stage of the machine on an integrated video monitor such as a Liquid Crystal Display panel equipped with crosshairs or similar reference marks. The XYZ stage of the host machine is used to move the part so that various features of the part are brought into the crosshairs of the video monitor. In such a way the XYZ coordinates of various features of the part with respect to a selected reference feature, displayed on the host machine's position readout, can be obtained. This procedure can be used to aid work piece setup, measure parts in-process without disturbing the setup, or to inspect finished parts for dimensional accuracy.

Figure 1A:
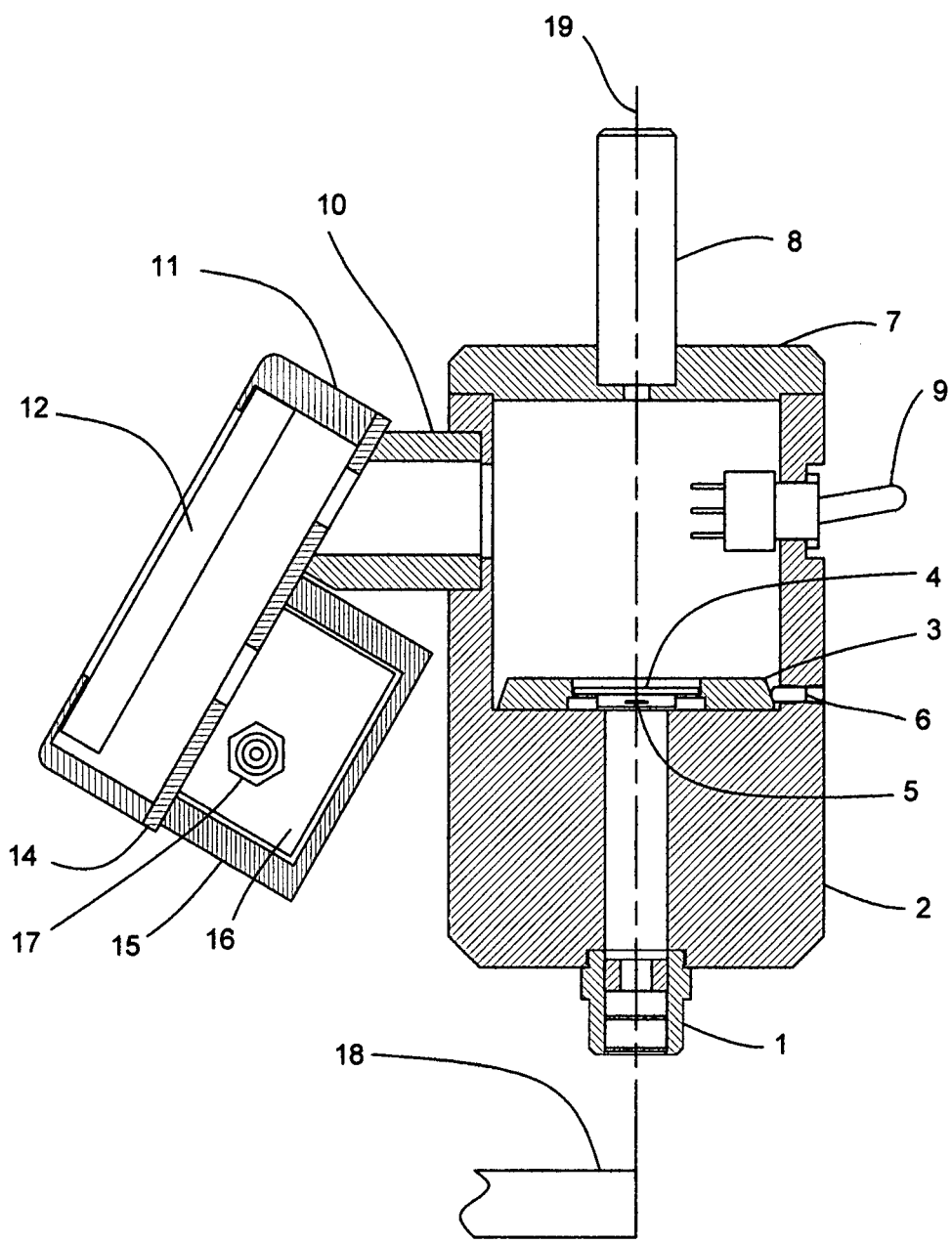

If a known good part or a specially manufactured precision gage plate is inspected by a host machine in such a way, the result is reflective of the accuracy of the XYZ stage and position display of the host machine and can be used to qualify the host machine for positional accuracy.

8 Claims, 3 Drawing Sheets

VIDEO IMAGING DEVICE WITH AN INTEGRATED BATTERY

CROSS-REFERENCE TO RELATED APPLICATIONS

This application claims the benefit of provisional patent application Ser. No. 60/802,664, filed 2006 May 23 by the present inventors.

FEDERALLY SPONSORED RESEARCH

Not Applicable

SEQUENCE LISTING OR PROGRAM

Not Applicable

BACKGROUND

1. Field of Invention

The field of the present invention relates to the inspection of manufactured parts. Specifically, firstly it relates to the inspection of finished parts for dimensional accuracy. Secondly, it relates to inspecting the host machine itself for positional accuracy.

2. Prior Art

Milling machines, jig borers, and similar machinery are used to work a piece of raw material into a part of a precisely specified geometrical shape. Such machinery usually has a rotating spindle and a way of securely holding a tool, such as a drill bit or an end mill, co-axial with said spindle. The work piece is securely held on a precision XYZ stage of such a machine and advanced a known distance against the cutting tool, removing material from the work piece. XYZ stages in these machines are equipped with means of displaying accurate coordinates of the stage's position.

A related prior art device for use in above described machines is the centering microscope. The centering microscope has been referred to as a well known prior art device in 1939 (U.S. Pat. No. 2,146,906 by Moller). The centering microscope consists of a microscope objective, a deflecting prism or mirror, and an eyepiece. The centering microscope also possesses an adapter that enables it to be mounted in spindles of machines. By viewing through the eyepiece, the operator sees a magnified image of the work piece, superimposed with crosshairs. When used in a host machine, crosshairs of a properly aligned centering microscope mark the axis of rotation of the spindle of the host machine (machine axis). A centering microscope is generally used to set up a work piece in a host machine by positioning the machine axis of the machine in a specific position on the work piece. In principle, using the centering microscope one can line up a particular feature of the part held in the host machine, note the position of the XYZ stage, line up another feature of the part on the crosshairs and note coordinates of the XYZ stage for that position, etc., and thus use the centering microscope to dimensionally inspect the part in the host machine. But the centering microscope requires operators to bring their heads down and look through the eyepiece. This position is incompatible with operating the host machine. One could use a standard eye piece adapter for a video camera. That would alleviate the problem of simultaneously viewing the part and operating the machine. But it would introduce into the setup a number of wires, for power, for video signal, for illumination, making it highly cumbersome to set up and highly inconvenient to use. Raiha in U.S. Pat. No. 4,438,567 (1984) describes a variation of the centering microscope that works in reverse by projecting a spot from an internal light source onto the work piece. The spot marks the machine axis and thus could be used in the same way as a centering microscope. The benefit would be that the user does not have to view through the eyepiece. The downside is that the accuracy of the positioning is limited to what an unaided eye can see.

A variety of stand-alone optical inspection equipment exists in the marketplace. These devices derive from layout machines such as the one described by Hawkes in U.S. Pat. No. 1,370,645 (1921). A part is placed on a tray and a pointed probe is moved around on a precision XYZ stage. The point of interest on the part is touched with a point on the probe and the coordinates of the position are read out from the stage. In one line of development the pointed mechanical probe has later on been replaced with a video camera equipped with the equivalent of a microscope objective. A digital readout of the position of the stage along all three axes is usually provided. In some versions of these machines the piece to be inspected is placed onto a XYZ translation stage while the camera is stationary. A particular feature of the part is aligned with the crosshairs integrated into the display device (such as a computer monitor) that displays a magnified image of a selected portion of the inspected part. By noting the numerical position along the three axes of the XYZ stage, as displayed on the digital readout, one can measure geometrical features of the inspected part with high precision. This stand-alone device is referred to as a Video Coordinate Measuring Machine (CMM). It is expensive and requires adequate floor space. Not every machine shop can afford it or has adequate space for it. Also, to inspect a part while in process of being machined, the part has to be taken out of the setup and brought to the CMM for inspection.

Another type of a CMM device uses an electronic touch probe instead of a video camera. The operation of these devices is conceptually similar to the video CMMs. The difference is that a part feature has to be touched with a probe rather than imaged onto crosshairs. Once the probe touches the part, the machine records the XYZ coordinates of the probe and converts them into the coordinates of the touched feature of the part. These devices, called touch probing CMMs, are also expensive and require a clean environment. Touch probes exist that can be operated in touch probe enabled milling machines (typically high end CNC milling machines). These probes can be used to inspect either in-process or finished parts. Touch probing is a useful and convenient method of inspection, but it is limited to those features that can be touched. Tiny holes, shallow steps etc. are examples of features that can not be touched.

CMMs described in this section exemplify the need for and the usefulness of dimensionally inspecting parts. These devices are typically used in QC departments away from the shop floor. Touch probes for use in touch probe enabled machines clearly indicate the need to bring inspection technology onto the production shop floor and into the production machines. Touch probe enabled machines represent a small fraction of machine tools currently in use.

SUMMARY

The present invention provides a compact, self-contained video imaging device for use in XYZ stage equipped host machines. The video imaging device comprises firstly an optical imaging component such as a microscope objective, secondly an electronic camera, thirdly a video monitor such as a Liquid Crystal Display (LCD) panel, fourthly an illumination providing device and fifthly a battery to provide power for the electronic components. These components are placed in a housing that is equipped with the standard means for mounting it into the host machine.

The video monitor is equipped with crosshairs to mark a position on the image. The video imaging device of the present invention converts the host machine into an optical inspection device by co-opting the existing precision XYZ stage and numerical position display of the host machine. Alternatively, for computer controlled machines, the video signal from the electronic camera could be wirelessly broadcast to the computer controlling the movements of the machine for image display and/or image analysis. This particular embodiment of the present invention may or may not have an integral video monitor. The imaging device of the present invention can also be used as a video probe in touch probe based CMMs. It can also be put on a stand or attached in an articulated arm and used as a video magnifier to visually inspect small parts or small features on large parts. However, it's most prevalent application is expected to be in standard production machines such as mills, jig borers, etc. A precision gage plate with a set of features at precisely known positions is used to qualify the host machine i.e. to confirm that the XYZ stage and the numerical position display of the host machine are sufficiently accurate for the intended inspection and machining functions.

DRAWINGS

Figures

Figure 1B:
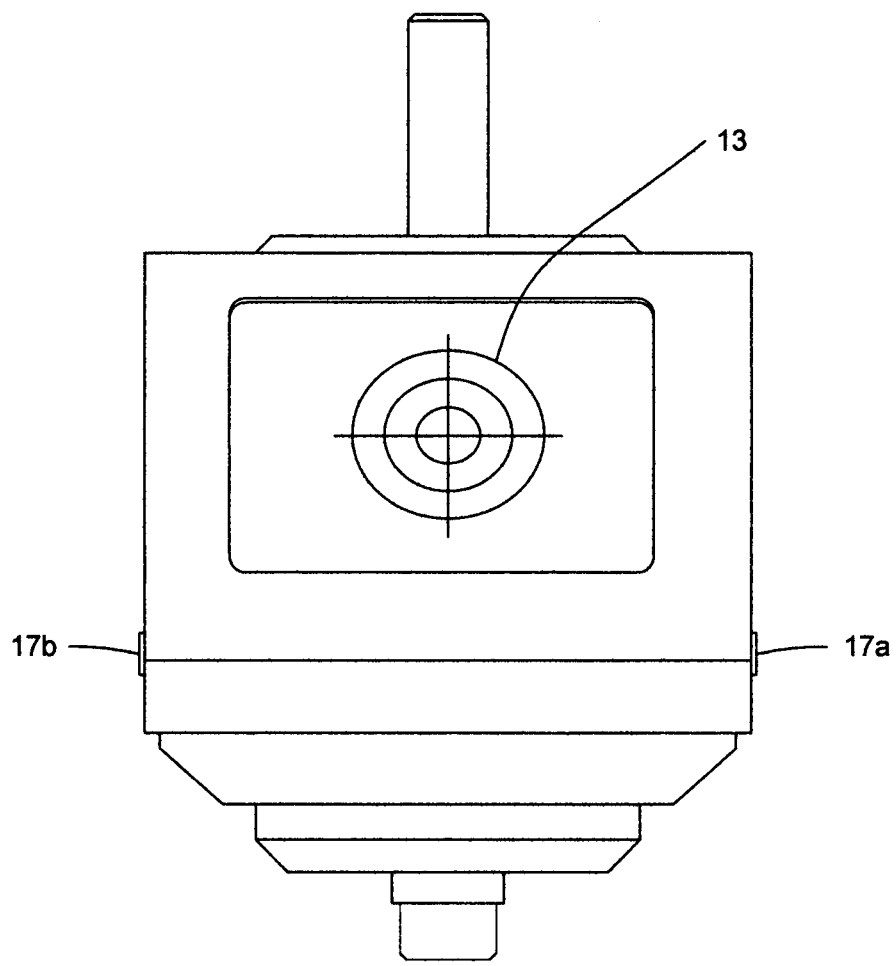
Figure 2:
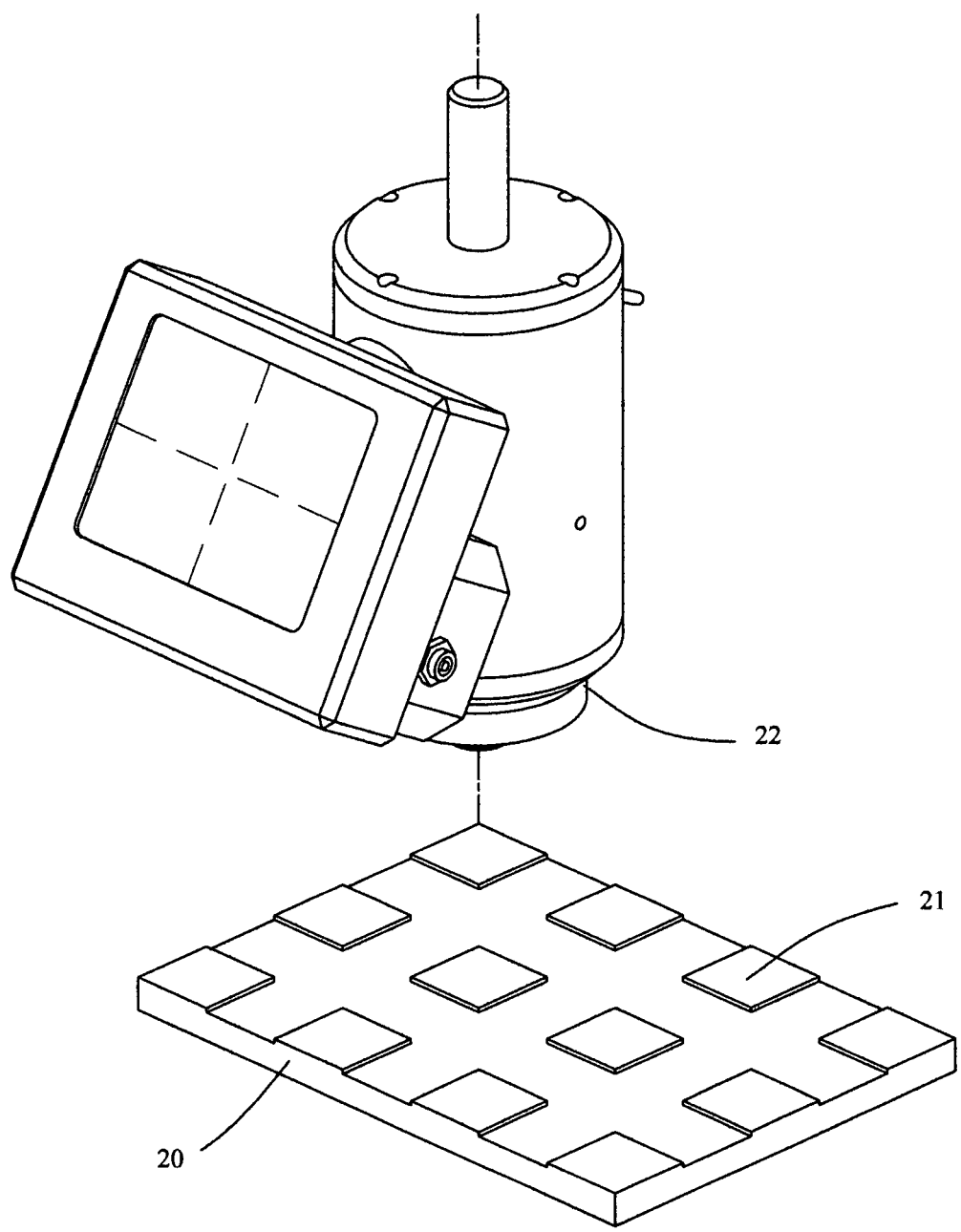

FIG. 1A shows a partial cross section of a side view of a basic embodiment.
FIG. 1B shows the front view of a basic embodiment.
FIG. 2 shows a basic embodiment with a gage plate.

DRAWINGS

Reference Numerals

1 Optical imaging component
2 Body
3 Camera holder
4 Electronic camera
5 Image sensor
6 Alignment screws
7 Cover
8 Shaft
9 Switch
10 Tubular member
11 Monitor housing
12 Video monitor
13 Crosshairs
14 Back wall
15 Battery enclosure
16 Battery
17a Connector A
17b Connector B
18 Object plane
19 Machine axis
20 Gage plate
21 Raised Square
22 Illuminator

DETAILED DESCRIPTION OF THE PREFERRED EMBODIMENTS

FIG. 1A illustrates a basic embodiment. An optical imaging component 1 (lens or microscope objective) is attached coaxially to the body 2 of the video imaging device. The body has a large counter bore machined into it from the opposite side of the optical imaging component 1. A camera holder 3 is positioned onto the bottom of the counter bore. An electronic camera 4 is mounted into the camera holder 3 with its image sensor 5 facing the optical imaging component. Three alignment screws 6 positioned circumferentially around the body determine the position of the camera holder 3, and thus the position of the image sensor of the camera, with respect to the axis of the device 19. The camera holder 3 has a beveled edge around the circumference so that a fraction of the force of the screws 6 pushing against the beveled edge is used to press the camera holder against the bottom of the counter bore. A bore through the center of the body lets light from the optical imaging component 1 to reach the sensor of the camera 5. The top of the body is enclosed by a cover 7 coaxial with the body thus enclosing a cylindrical chamber inside the body. A hardened steel shaft 8 is rigidly and coaxially attached to the cover. An electrical on/off switch 9 is mounted into the chamber wall in such a way to enable the switch to be operated from the outside, but having all the electrical connections inside the body.

One side of a tubular member 10 is rigidly attached to the chamber wall while the other side supports an enclosure or housing 11 for a video monitor 12. The other side of the tubular member could be cut at an angle to the axis of the tubular member so that the video monitor is mounted tilted upward for easier viewing when mounted in a host machine. The monitor housing 11 has a large opening on the side opposite to the one facing the body to match the screen of the video monitor. The monitor is attached and sealed into the monitor housing with the screen facing and visible through the opening. The screen is preferably covered with a thin clear plastic sheet (such as a Mylar sheet) for protection, the plastic sheet having crosshairs 13 or other position indicating markings on the side facing the screen.

The back wall 14 of the monitor housing 11 has a hole to match a hole through the tubular member 10 that allows access from the enclosed chamber into the body through the tubular member to the monitor housing. A battery enclosure 15 that houses a battery 16 is attached to the outside of the back wall of the monitor housing. Another hole in the back wall of the monitor housing enables access from the battery enclosure into the monitor housing. The described arrangement enables electrical wires to internally connect the electronic camera 4, the video monitor 12, the battery 16 and the switch 9, while keeping the interior of the device protected from outside elements such as dust. Two connectors 17a and 17b are mounted into the walls of the battery enclosure 15. One of the connectors is for the recharging of the battery; the other provides power for a detachable illuminator 22. The detachable illuminator could be of a standard ring type with the center hole matching the outside diameter of the optical imaging component 1 so it can be quickly slid around the optical imaging component, secured to it (for instance with a screw), and powered from one of the connectors.

The optical imaging component 1 possesses an object plane 18 and an image plane which is designed to coincide with the position of the camera's image sensor 5. For an object placed in the object plane, an image of the object is projected onto the image sensor in the image plane. The image recorded by the camera is displayed on the video monitor.

By advancing one of the screws 6 and simultaneously backing one of the other two, the camera mount can be moved within the image plane. One of the set screws can be replaced with a standard spring plunger so that, within a range of the spring plunger, the camera holder can be moved using two screws and the plunger follows these motions by always keeping the camera holder pushed against the two screws.

Each individual picture element on the image sensor corresponds to a unique picture element on the monitor. By adjusting the position of the camera using screws 6, the image sensor could be placed in a position in which the picture element of the image sensor that corresponds to the picture element in the crosshairs of the video monitor coincides with the image of the machine axis 19 in the object plane. To achieve the alignment of the machine axis of the host machine with the crosshairs of the monitor, the camera is adjusted in the image plane until a point in the object plane, independently known to be exactly on the machine axis, is brought into the crosshairs.

Since the video imaging device mounts into a production machine tool, the host machine can be quickly switched between production and inspection functions. The video imaging device has several distinct uses.

It is very important for a machining operation that the machine operator knows very precisely the position of the machine axis on the work piece. In one of its intended utilizations the video imaging device is mounted in the spindle of a machine tool such as a vertical milling machine. The hardened shaft 8 is chosen to fit in standard tool holders, chucks, collets, etc. If the surface of the work piece is brought into the object plane of the video imaging device, a magnified image of the work piece appears on the video monitor. If the video imaging device is properly aligned, the crosshairs mark the position of the machine axis on the work piece. This way, by moving the work piece using the X and Y stages of the host machine, the machine axis could be precisely placed onto any feature on the top surface of the work piece. Since the setup is based on observing the visual features of the work piece, even the features on the work piece that can not be touched such as tiny steps, tiny holes, scribed or engraved markings, etc. can be used for the setup. Also, both X and Y coordinates are set at the same time.

A next utilization is the inspection of a part that is in-process of being machined. The critical features of the work piece can be verified directly in the machine before dismantling the setup. Features of interest are brought into the crosshairs of the video monitor by moving the part in the XYZ stage of the host machine, noticing the coordinates of the features on the position readout of the host machine and comparing them with the print of the part.

Next and a related utilization is the inspection of a finished part. This is similarly done by lining up various features of the part with crosshairs and noting their coordinates on the digital position readout of the host machine just as it is done in a standard video CMM. Note however that a standard video CMM can not be used to aid the set up of a work piece in a machine tool or to do in-process, in-setup inspection of the work piece. In addition, the size of the part that can be inspected in a CMM is limited by the length of its X, Y and Z stage motions. With the video imaging device of the present invention the size of the part that can be inspected is the same as the size of the part that can be produced since both operations are performed in the same machine tool. Also, the video imaging device of the present invention is expected to cost considerably less than a conventional CMM.

The described measurement and inspection functions of the video imaging device are predicated on the assumption that the positional accuracy of the host machine is appropriate for the required operations. Machine tools can and do go out of calibration and the measurements as well as the production done by out of calibration machine tools could become inaccurate. Another key aspect of the present invention is a precision gage plate that allows the positional accuracy of the host machine tool to be quickly assessed. FIG. 2 shows the use of the present invention with the precision gage plate 20. The gage plate features a grid of raised squares 21 arranged in a checker-board pattern. The advantage of the raised squares over an engraved gridline pattern is that the gridlines must have some width and thus the centering of the crosshairs on the gridlines is always somewhat uncertain. Raised squares have edges that are without width. Similarly, a checkerboard pattern of two different color squares could be engraved on a plate. The border between two differently colored squares would similarly be without width. For the convenience of inspection, the squares could have sides exactly 1.000" and could be exactly 1.000" apart. Obviously, the sides and spacing other than 1.000" can be used and they may be different along different axes, in which case the squares would become rectangles. The positional accuracy of a host machine tool could be easily assessed by inspecting the gage plate in the host machine. Since the gage plate is known to be accurate, if the inspection yields any deviations of the measured plate dimensions from nominal dimensions, these deviations are due to the positional inaccuracy of the host machine. A gage plate made of metal is convenient because it could be easily placed and tightened in a machine vise. Metals change dimensions with temperature so the temperature at which the gage plate can be used has to be specified (for example 70° F.). The dimensional change with temperature however is very predictable for metals and the gage plate can be used at other temperatures providing the appropriate corrections are applied. There are materials (Zerodur, Constantan, quartz, etc.) that have a very low coefficient of thermal expansion and it would be obviously advantageous to make the gage plate out of these materials. However, in most cases a gage plate made of aluminum or steel is adequate if the temperature of the plate is taken into account.

In another embodiment, a video signal from the camera is wirelessly transmitted to a computer that controls movements of the host machine tool. The computer also has software for image analysis. A number of commercially available image analysis software packages are available. The image analysis software provides feedback to the software that controls the machine movements based on images received from the camera. To inspect that a part is made to print, the machine moves the part so that successive features of the part are displayed on the computer monitor. Image analysis software compares observed features to the print and records any variances observed. The software compares measured variances with tolerances allowed for the specific features and provides an inspection report for the part. In this way, a fully automated, operator free inspection is performed. This embodiment may or may not have an integral video monitor.

In yet another embodiment the video imaging device of the present invention could be mounted on a stand and used as a magnifier to visually inspect small features. Instead of the stand, the video imaging device could be mounted in an articulated arm so the video imaging device could be moved around allowing the inspection of small features on a large part.

The important advantage of the present invention over previous art is the integration of an electronic camera, a video monitor, a battery and an illumination source into a single device. Because these components are integrated into a single unit, there are no connecting wires that could become entangled into the XYZ stage movements. Also, it makes the insertion of the video imaging device into the host machine a task that takes just a few seconds.

Another important advantage is the use of the gage plate to pre-qualify the host machine tool for positional accuracy. There are a number of quality programs, such as ISO 9000, that production companies are eager to comply with in order to reassure their customers about the quality and consistency of their production output. These programs require that machine tools be periodically checked for positional accuracy.

While the present invention has been described in connection with a basic embodiment, it will be understood that modifications thereof within the principles outlined above will be evident to those skilled in the art and thus the invention is not limited to the basic embodiment but is intended to encompass such modifications.

We claim:

1. A video imaging device for use in XYZ stage equipped machine tools comprising:
    an optical imaging component and an electronic camera coaxially arranged in a common housing with the image sensor of said electronic camera placed in the image plane of said optical imaging component,
    a video monitor connected to said electronic camera and attached to said housing,
    a battery attached to said housing providing power to said electronic camera and said video monitor,
    said device having a means to mount into tool holder of said XYZ stage equipped machine tool by standard means, so that an object placed onto said XYZ stage can be moved in a precise and controlled way in the object plane of said optical imaging component and a magnified image of said object displayed on said attached video monitor;
    wherein said video monitor incorporates crosshairs and the position of said crosshairs is adjustable to mark the position of a spindle axis of a host machine on a work piece, whereby enabling setup of said work piece in said host machine as well as in-process inspection of said work piece without disturbing said setup.

2. The video imaging device of claim 1 where a source of illumination is integrated into said device and powered by said integral battery.

3. The video imaging device from claim 1 where the signal from said camera is sent wirelessly to a remote computer for image display and/or analysis.

4. The video imaging device from claim 1 where the electronics of said camera enables electronic zoom.

5. The video imaging device from claim 1 used in a host machine in conjunction with a gage plate, said gage plate having a set of visual features in precisely known positions, said visual features being in a precise relationship to the external dimensions of said gage plate, said features being either of different color, or at a different height, so that the border between said features is clearly visually defined, but has no width so that said gage plate together with said video device can be used for the purpose of qualifying the positional accuracy of said host machine.

6. A video imaging device for use in XYZ stage equipped machine tools comprising:
    an optical imaging component and an electronic camera coaxially arranged in a common housing with the image sensor of said electronic camera placed in the image plane of said optical imaging component, wherein the signal from said camera is broadcast wirelessly to a remote computer monitor for image display and analysis,
    a battery attached to said housing providing power to said electronic camera,
    a means to mount said video imaging device into said XYZ stage equipped machine tool via standard means, whereby said video imaging device produces a magnified image of an object placed in the object plane of said optical imaging component on said computer monitor;
    wherein said computer monitor incorporates crosshairs and the position of said crosshairs is adjustable to mark the position of a spindle axis of a host machine on a work piece, whereby enabling setup of said work piece in said host machine as well as in-process inspection of said work piece without disturbing said setup.

7. The video imaging device of claim 6 where a source of illumination is integrated into said video imaging device and powered by said integral battery.

8. The video imaging device from claim 6 used in said host machine in conjunction with a gage plate, said gage plate having a set of visual features in precisely known positions, said visual features being in a precise relationship to the external dimensions of said gage plate, said features being either of different color, or at a different height, so that the border between said features is clearly visually defined, but has no width so that said gage plate together with said video device can be used for the purpose of qualifying the positional accuracy of said host machine.

* * * * *